United States Patent
Goodman et al.

[11] Patent Number: 5,817,522
[45] Date of Patent: Oct. 6, 1998

[54] SELF-CONTAINED ASSAY DEVICE AND METHOD

[76] Inventors: David B. P. Goodman, 1201 Grenox Rd., Wynnewood, Pa. 19096-2218; Michael B. Prystowsky, 263 Sterling Rd., Harrison, N.Y. 10528

[21] Appl. No.: 969,177

[22] Filed: Nov. 12, 1997

[51] Int. Cl.⁶ .......................... G01N 21/01; G01N 33/48
[52] U.S. Cl. ............................ 436/165; 422/61; 422/102
[58] Field of Search ................................. 436/164, 165; 422/58, 61, 102, 103

[56] References Cited

U.S. PATENT DOCUMENTS

| | | |
|---|---|---|
| 3,713,779 | 1/1973 | Sirago et al. .............................. 422/61 |
| 4,522,923 | 6/1985 | Deutsch et al. . |
| 4,608,231 | 8/1986 | Witty et al. . |
| 4,623,461 | 11/1986 | Hossum et al. . |
| 4,769,333 | 9/1988 | Dole et al. . |
| 4,837,159 | 6/1989 | Yamada . |
| 4,857,453 | 8/1989 | Ullman et al. . |
| 4,859,419 | 8/1989 | Marks et al. . |
| 4,859,421 | 8/1989 | Apicella . |
| 4,918,025 | 4/1990 | Grenner . |
| 4,978,502 | 12/1990 | Dole et al. . |
| 4,978,504 | 12/1990 | Nason . |
| 4,981,786 | 1/1991 | Dafforn et al. . |
| 5,078,968 | 1/1992 | Nason . |
| 5,137,808 | 8/1992 | Ullman et al. . |
| 5,147,780 | 9/1992 | Pouletty et al. . |
| 5,162,237 | 11/1992 | Messenger et al. . |
| 5,162,238 | 11/1992 | Eikmeier et al. . |
| 5,164,318 | 11/1992 | Sato et al. . |
| 5,169,789 | 12/1992 | Bernstein . |
| 5,288,463 | 2/1994 | Chemelli ................................... 422/61 |
| 5,501,837 | 3/1996 | Sayles ....................................... 422/61 |
| 5,639,424 | 6/1997 | Rausnitz ................................... 422/61 |

*Primary Examiner*—Lyle A. Alexander
*Attorney, Agent, or Firm*—Pennie & Edmonds LLP

[57] ABSTRACT

The assay device includes a first housing and a specimen holder rotatably fit in the first housing. The specimen holder has a center portion, a circular flange surrounding the center portion and a pin member extending from the underneath of the center portion. The center portion has a radial slot extending from its peripheral toward its center. A spring/latch assembly is adapted to be held in the slot on the specimen holder and includes a spring member disposed near the center of the center portion and a latch member having a remote end. The assay device also includes a second housing, preferably a cam plate fixedly fit in the first housing. The cam plate has a rim portion surrounding a concave portion adapted to accommodate the center portion of the specimen holder and an opening on the rim portion for adding a specimen to be tested. A plurality of cam-shaped chambers are provided in the rim portion and communicate with the concave portion. Each cam-shaped chamber has an apex portion located furthest away from the concave portion and a cam side extending from the apex portion toward the next chamber and each chamber has a capsule, retained therein, containing either a reagent or wash solution. When the specimen holder is rotated relative to the cam plate, the remote end of the latch member moves along the rim portion and thrusts into each chamber and breaks the capsule retained therein to release a reagent for testing an analyte(s) in a specimen.

17 Claims, 5 Drawing Sheets

SELF-CONTAINED ASSAY DEVICE AND METHOD

FIELD OF THE INVENTION

The present invention relates generally to a self-contained assay device, which is capable of detecting various analytes, including bioanalytes, in specimens, for example, from biological sources. More particularly, the present invention relates to a hand-held self-contained disposable assay device for a rapid and convenient detection of analyte(s) by the use of a specific binding pair, such as antibody/antigen, polynucleotide/complementary polynucleotide, ligand/receptor, enzyme/substrate and enzyme/co-factor, etc. The present invention further relates to a method of using the self-contained assay device.

BACKGROUND OF THE INVENTION

In testing blood or other fluid samples for medical evaluation and diagnosis, a rapid and simple assay is usually needed by medical professionals. Over the years, various devices and methods have been developed for assaying analytes in specimens of biological origin.

U.S. Pat. No. 4,522,923 discloses an apparatus containing a test tube with at least three chambers each containing different chemicals, including a solid sphere, and separated from each other by a water-soluble barrier.

U.S. Pat. No. 4,623,461 discloses a transverse flow diagnostic device containing absorbent means associated with the peripheral zone of a filter.

U.S. Pat. No. 4,608,231 discloses a self-contained reagent package device containing a plurality of wells in the support member.

U.S. Pat. No. 4,769,333 discloses a personal, disposable hand held diagnostic kit having specimen support member. The specimen support member carries a plurality of receptacles for containing liquid materials. The receptacles are later cut in sequence to release the liquid.

U.S. Pat. No. 4,837,159 discloses an automatic chemical analyzer including a turntable rotated intermittently at a constant pitch and holding a number of reaction vessels. U.S. Pat. No. 4,857,453 discloses a device for conducting an immunoassay containing a means in the housing for introducing a sample into the device and a self-contained liquid reagent in a breakable container.

U.S. Pat. No. 4,859,421 discloses a disposable antigen concentrator and detector containing a reagent storage chamber connected to the reaction chamber through a valve means which allows fluid flow from the reagent chamber to the reaction chamber.

U.S. Pat. No. 4,859,419 discloses an apparatus for immunoassay of multiple samples of biological fluids containing a frame having plural test vessels.

U.S. Pat. No. 4,918,025 discloses a self-contained immunoassay element including a capillary containing a fixed reagent in fluid communication with reagent reservoirs.

U.S. Pat. No. 4,978,502 discloses a device containing a molded, flexible blister having an open side and a structure for rupturing the blister closure in response to relative motion between the blister and test specimen support members.

U.S. Pat. No. 4,981,786 discloses a multiple port assay device containing a housing means for capturing a first member of a specific binding pair in a zone and for allowing liquid to be transported by capillary action away from the zone.

U.S. Pat. Nos. 4,978,504 and 5,078,968 disclose a specimen test unit containing a specimen collecting swab and a reagent-containing ampoule in cylindrical housing which can be bent or squeezed or otherwise deformed to fracture a reagent-containing ampoule.

U.S. Pat. No. 5,137,808 discloses a liquid reagent in a breakable container utilized for the determination of an analyte in a sample, and liquid reagents in a container which pass into a second container when a seal is ruptured.

U.S. Pat. No. 5,147,780 discloses an apparatus for the detection of analytes containing a liquid medium restrained from a sample absorbing nib by a frangible barrier which is broken allowing the nib to drop into the liquid medium.

U.S. Pat. No. 5,162,237 discloses an analytical reaction cassette for performing sequential analytical assays by non-centrifugal and noncapillary manipulations.

U.S. Pat. No. 5,162,238 discloses a test carrier for the analysis of a sample liquid containing a sample application zone, a covering mesh, an erythrocyte separation layer, two reagent layers and a liquid transport layer made of an absorbent material.

U.S. Pat. No. 5,164,318 discloses an automatic analyzer for performing immunoassays containing a sample carrying rotary disk supporting rotation of a plurality of sample cups for containing a sample.

U.S. Pat. No. 5,169,789 discloses a self-contained solid phase immunodiffusion assay containing a tube having a sample collector and compartmentalized reagents separated by seals which can be broken through pressure on the sample collector, mixed with reagent, and pushed into a ligand receptor reaction area.

There still remains a need in the art for a self-contained, inexpensive, disposable assay device for detecting an analyte member of a specific binding pair. More specifically, there is a need for an assay device that can be used easily and effectively by untrained personnel, preferably without the need for complex additional instruments to complete the detection of analyte. The present invention provides such an economical, compact, easy to operate and self-contained assay device for detecting an analyte in a sample, such as a biological sample, which meets the requirements.

SUMMARY OF THE INVENTION

The present invention relates to a self-contained assay device which is capable of detecting various analyte(s), including bioanalytes, in specimens from various sources such as a biological source, an ecological source, a toxic industrial source, etc. The assay device includes a first housing and a specimen holder rotatably fit in the housing. The specimen holder has a center portion, a circular flange surrounding the center portion and a pin member extending from underneath of the center portion. The center portion has a radial slot extending from its peripheral toward its center. A spring/latch assembly is adapted to be held in the slot on the specimen holder and includes a spring member disposed near the center of the center portion and a latch member having a remote end.

The self-contained assay device according to the present invention also includes a second housing fixedly fit in the first housing. The second housing is preferably a cam plate and has a rim portion surrounding a concave portion adapted to accommodate the center portion of the specimen holder. The cam plate also includes an opening on the rim portion for adding a specimen to be tested. A plurality of cam-shaped chambers are provided in the rim portion and communicate with the concave portion. Each cam-shaped chamber has an apex portion located furthest away from the concave portion and a cam side extending from the apex portion toward the next chamber. When the specimen holder is rotated relative to the cam plate, the remote end of the latch member moves along the rim portion and can be thrust into each chamber to break open a reagent packet to release a reagent or wash solution contained therein for use in testing for the presence of an analyte in a specimen.

The cam plate, the specimen holder, the latch member and the housing of the self-contained assay device can all be made of clear or transparent material, such as acrylic. The advantage of using such a transparent material is that it is easy for the user to observe the reactions carried out in the assay device. In a preferred embodiment, the above-mentioned components are made of color plastic. Moreover, the specimen holder can be made of cloudy plastic.

The self-contained assay device of the present invention can further comprise first and second retainer members which are located in the rim portion of the cam plate and determine a start position and an end position of the assay device. The first retainer member is preferably located in the same radial direction of the opening of the cam plate. In a preferred embodiment, the first and second retainer members are nitch and slot members.

The number of the cam-shaped chambers can be from 2 to 8 and preferably from 4 to 6. In a preferred embodiment, there are four cam-shaped chambers. The apex portions of these chambers and the first and second retainer members are evenly distributed along the rim portion.

The self-contained assay device of the present invention can further comprise a blotter member inserted between the bottom of the housing and the specimen holder. A receptacle can be adopted to be attached to the opening of the cam plate for introducing a specimen into the assay device. A knob member is used to provide grip mechanism for the rotation of the assay device. The knob member has a center hole for fixedly fitting onto the pin member of the specimen holder. In addition, the remote end of the latch member can be a curved tip portion to facilitate the relative rotation between the specimen holder and the cam plate. The spring member is a compressed spring.

In a preferred embodiment, each chamber has a recess portion at its apex portion for retaining a capsule therein. Alternatively, a retaining plate can be used which has a hollowed-out center and adapted to fit onto the circular flange of the specimen holder. The retaining plate has a through hole and a plurality of recess portions corresponding to the opening and the apex portions of the cam plate. The recess portions on the retaining plate are adapted to retain capsules therein.

The present invention also relates to a method for detecting an analyte in a specimen. The detecting method comprises the steps of: (a) providing a self-contained assay device as described herein above, (b) adding a specimen of a predetermined quantity into the assay device through the opening on the cam plate, (c) rotating the specimen holder relatively to the cam plate to move the spring/latch assembly from a start position toward a first chamber till the spring/latch assembly reaches the first chamber to break a capsule retained therein releasing a reagent or wash solution contained within the capsule, (d) rotating the specimen holder relatively to the cam plate to move the spring/latch assembly to the next chamber to break a capsule retained therein releasing a reagent or wash solution contained within the capsule, (e) repeating the above step (d) till the spring/latch assembly reaches the last chamber and breaks a capsule retained therein, (f) rotating the specimen holder relatively to the cam plate to move the spring/latch assembly from the last chamber to an end position and (g) observing the results to determine the presence or absence of the analyte(s) in the specimen.

BRIEF DESCRIPTION OF THE DRAWINGS

These and other features, aspects, and advantages of the present invention will become much more apparent from the following description, appended claims, and accompanying drawings, in which:

FIGS. 5a and 5b are top and side views of the latch member in the self-contained assay device in FIG. 1;

DETAILED DESCRIPTION OF THE PREFERRED EMBODIMENTS

Figure 1:
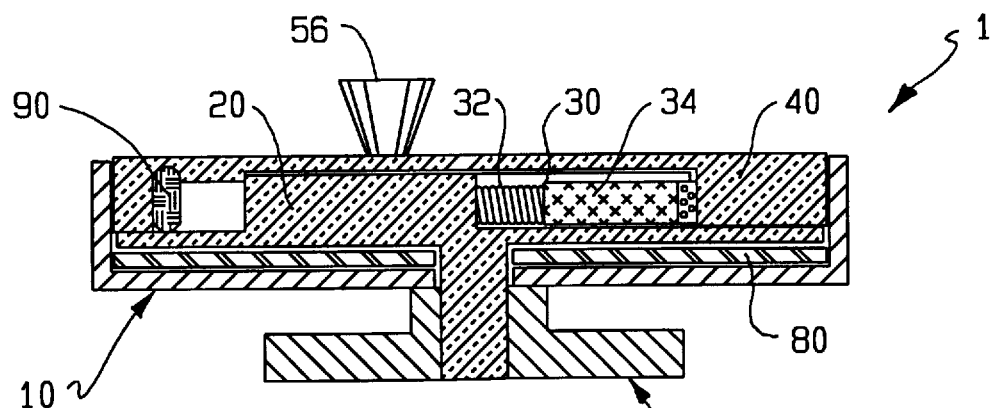
FIG. 1 is a cross-section of the first embodiment of a self-contained assay device of the present invention.

Various self-contained assay devices embodying the principles of the present invention are illustrated in FIGS. 1–15. Such self-contained assay devices have a compact structure and are inexpensive to make. Therefore, they can be easily carried for conducting rapid detection of analytes on site and be conveniently discarded after use. In each embodiment, the same elements are designated with the same reference numerals and repetitive descriptions are omitted.

Referring to FIG. 1, a self-contained assay device 1 of the present invention is shown in cross-section. The self-contained assay device 1 has a first housing 10 for encasing a specimen holder 20 containing a spring/latch assembly 30. A second housing 40, preferably a cam-plate, is provided to be tightly fit with the first housing 10 and thus fixed thereto, while the specimen holder 20 and the second housing 40 are rotatable relative to each other. The spring/latch assembly 30 is adapted to move radially in the assay device 1. The cam-plate 40 has an opening 54 (FIG. 6a) thereon for introducing a specimen into the assay device 1.

When the specimen holder 20 and the cam-plate 40 are made to rotate relative to each other, the spring/latch assembly 30 can move radially outwardly to break a reagent packet 90 contained in the self-contained assay device 1. Thus, the reagent released from the packet 90 can react with the added specimen for analysis purposes. The reagent packet 90 can be in various forms such as capsules, packets or the like, even though FIG. 1 shows a capsule 90 in specific.

Figure 2A:
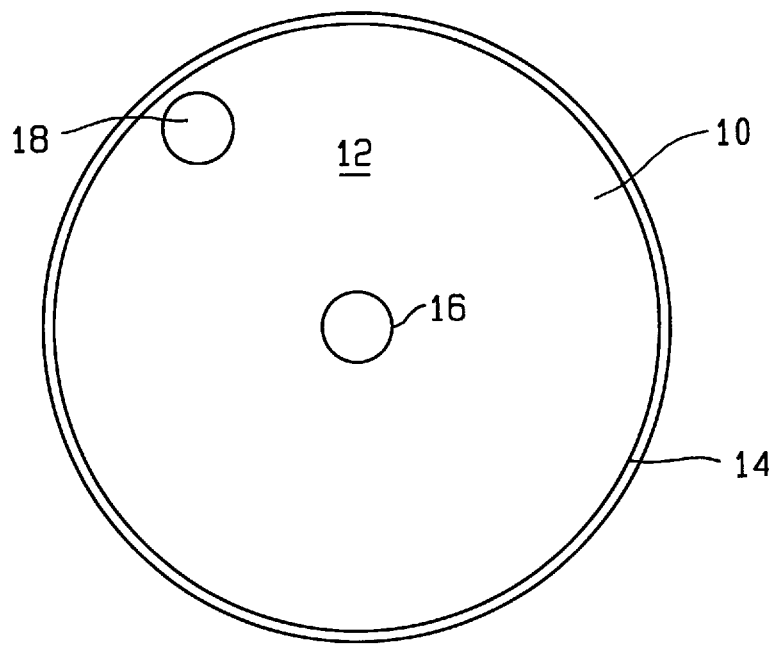
FIGS. 2a and 2b are top and side views of the first housing in the self-contained assay device in FIG. 1.
Figure 2B:
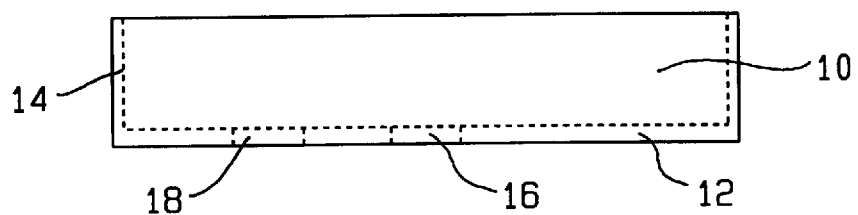

As shown in FIGS. 2a and 2b, the first housing 10 of the assay device 1 consists of a bottom plate 12 and an upstanding wall 14. The upstanding wall 14 has a height so that the first housing 10 can accommodate both the specimen holder and the cam plate as will be described later. Preferably, the bottom plate 12 has a circular shape and thus the upstanding wall 14 is also circular. A through hole 16 is formed in the center of the bottom plate 12 for passing a pin member on a specimen holder as will be described later.

The first housing 10 of the assay device 1 can be made of various materials and by various processes. Materials, such as plastics, are preferred for their inexpensive cost and non-erosive features. In an embodiment, the first housing 10 is molded or otherwise fabricated of clear or transparent plastic material. Acrylic is one illustrative non-limiting example of a suitable plastic material. As will be understood by those skilled in the art, any of a number of other polymeric plastic materials are suitable for fabricating the assay device of the present invention. One advantage of using such a transparent plastic material is that it is easier for the user to visually observe, with an unaided eye, the elements housed in the first housing 10 and to determine whether a chemical reaction or binding has occurred in the assay device 1.

In an alternative embodiment, the first housing 10 has a through hole 18 provided on its bottom plate 12 and near its upstanding wall 14. Such through hole 18 is designed to assist the user in observing the final result of the assay reactions. The through hole 18 is particularly needed when the housings 10 and 40, the specimen holder 20 and the blotter member are non-transparent. As will be described later, the through hole 18 and other openings or apertures on the second housing 40 and the blotter member are properly oriented upon assembly so that they will be aligned at an end position of the assay device 1.

Figure 3A:
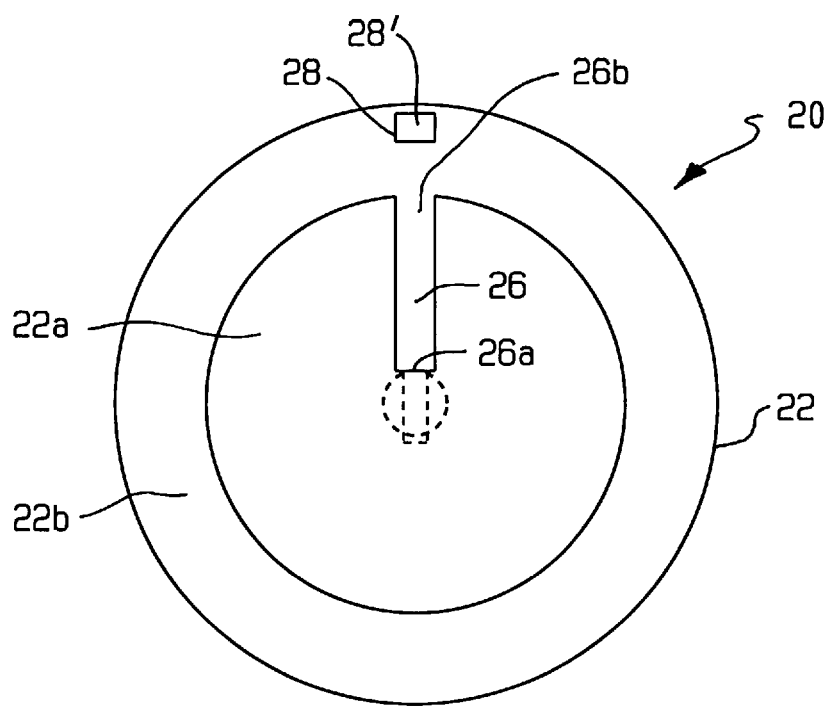
FIGS. 3a and 3b are top and cross-section views of the specimen holder in the assay device in FIG. 1.
Figure 3B:
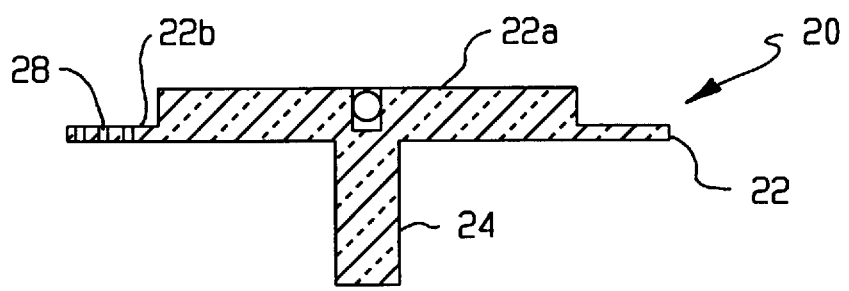

The specimen holder 20, as shown in FIGS. 3a and 3b, is in the shape of a circular plate 22 with a pin member 24 extending from underneath and at the center thereof. The circular plate 22 is dimensioned to be loosely fit and freely rotatable inside the upstanding wall 14 of the first housing 10 after assembling. The specimen holder 20 can also be made of various materials and by various processes. Similar to that with the first housing 10, materials, such as polymer plastics, are preferred for making the specimen holder 20. In a preferred embodiment, the specimen holder 20 is molded of clear acrylic either with or without color. Moreover, the specimen holder 20 can be made of cloudy plastic.

In the current preferred embodiment, the circular plate 22 is stepped to form a center portion 22a and a circular flange 22b surrounding the center portion 22a. The center portion 22a has at least one slot 26 extending radially from its periphery toward its center for accommodating a spring/latch assembly 30 as will be described later. The slot 26 has a closed end 26a located near the center of the circular plate and open end 26b near the periphery of the center portion 22a. The number of the slot 26 can be one or more depending on the nature of the test assays to be performed using the assay device.

One main function of the circular flange 22b is to hold the specimen to be examined and/or other analyte(s) and reagent (s). As will be described later, the added specimen is deposited on the circular flange 22b of the specimen holder 20 at a position at which the slot 26 opens. Such position is designated by reference numeral 28 in FIG. 3a. In a preferred embodiment, at least the portion of the circular flange 22b where position 28 is located is made of a porous material. In this manner, any unbound specimen or reagent can pass therethrough after each reaction or washing process and be deposited on a blotter member as will be discussed hereinafter.

Figure 4A:
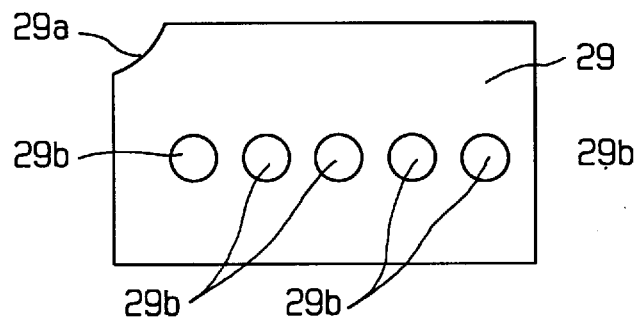
FIGS. 4a and 4b show a plane view of the membrane member and a side view of the specimen holder with the membrane member attached to it.
Figure 4B:
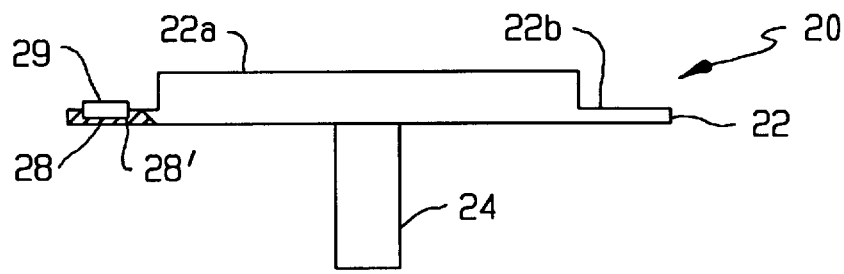
Figure 5B:
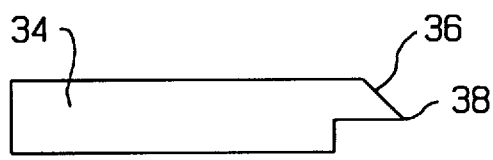
Figure 5B:
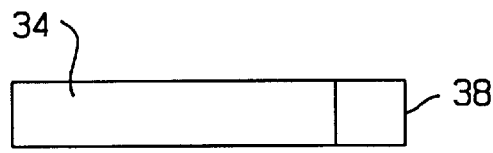

In an embodiment, a membrane member 29 (FIG. 4a) can be provided on the circular flange 22b of the specimen holder 20 at position 28, as shown in FIG. 4b. The membrane member 29 is made of a porous material including but not limited to such as nitrocellulose. In addition, the position 28 on the specimen holder 20 has pores or channels similar to those described above to allow liquid to pass therethrough. Thus, unbound specimen or reagent is allowed to pass through the membrane member 29 and position 28 onto the blotter member 80, while the bound specimen or reagent 90 is immobilized by the membrane member 29 for subsequent reaction or examination as will be discussed hereinafter.

The membrane member 29 can be retained in place through various conventional methods such as adhesion, embedment and insertion, etc. In the preferred embodiment as shown in FIG. 3a, the circular flange 22b of the specimen holder 20 has a cut-out portion 28' at position 28. The cut-out portion 28' can be in the form of a through hole. Thus, the membrane member 29 is inserted in the cut-out portion or the through hole 28' and retained therein.

In certain embodiments, such as shown in FIG. 4a, the membrane member 29 can have a plurality of areas or zones 29b. Such areas or zones 29b are capable of immobilizing one member of a specific binding pair, which is complementary to the analyte(s) to be detected, to serve as a "capture site" for any analyte in the specimen. For example, if the analyte to be detected is an antibody, the antigen to which the antibody binds specifically can be immobilized on a predetermined area or zone, 29b, of the membrane member 29. As another example, if the analyte to be detected is an antigen, an antibody to which the antigen binds specifically can be immobilized on a predetermined area or zone, 29b, of the membrane member 29.

Further, the membrane member 29 can be used to immobilize not only the specimen and/or a member of the specific binding pair but also one or more reagents which can serve as a positive or negative control. For a positive control, the membrane member 29 has a predetermined amount of the analyte(s) to be detected immobilized on a predetermined area or zone 29b of the membrane member 29. For a negative control, the membrane member 29 has a predetermined amount of a substance to which the analyte does not bind specifically immobilized on a predetermined area or zone 29b of the membrane member 29.

FIG. 4a shows a number of areas or zones 29b at which the appropriate substance to serve as a positive or negative control and other tests can be immobilized. The areas or zones 29b shown in FIG. 4a are presented for illustrative purposes only and, as will be understood by those skilled in the art, the size and configuration of the areas or zones 29b is a matter of design choice.

In addition, the number of areas or zones 29b depends upon the number of analytes to be assayed using the device. For example, as shown in FIG. 4a, the areas or zones 29b can have immobilized positive control reagents for 5 different assays. Alternatively, the zones or areas 29b can have immobilized one substance for a negative control and 4 positive control reagents. FIG. 4a is presented for illustrative purposes only and the determination of the size, number and configuration of the areas or zones 29b are well within the skill in the art.

Additionally, the membrane member 29 can be configured so that the portions of the membrane member 29 represented by the areas or zones 29b can be properly oriented in a predetermined orientation. In a preferred embodiment, a cut-out portion 29a (FIG. 4a) can be provided on the membrane member 29 to assist in orienting the membrane member 29 during manufacturing and assembling. Other orientating mechanism as can be contemplated by those skilled in the art can also be used.

The spring/latch assembly 30 consists of a spring member 32 (FIG. 1) and a latch member 34 (FIGS. 5a and 5b), both adapted to be fit in the slot 26 on the specimen holder 20. The spring member 32 is disposed at the closed end of the slot 26 near the center of the specimen holder 20 while the latch member 34 is arranged adjacent to the spring 32 and has a remote end 36 pointing outwardly. It is preferred that the spring member 32 is a compression spring. The compression spring 32 is kept in its compressed state before use. The remote end 36 of the latch member 34 is preferably curved to conform with a curved apex portion of the cam-shaped chamber as will be described hereinafter and therefore break a reagent packet 90 retained at the curved apex portion more efficiently. The curved end 36 is further cut to form a tip portion 38 for fitting in a retaining mechanism at start and end positions as will be described later.

Figure 6A:
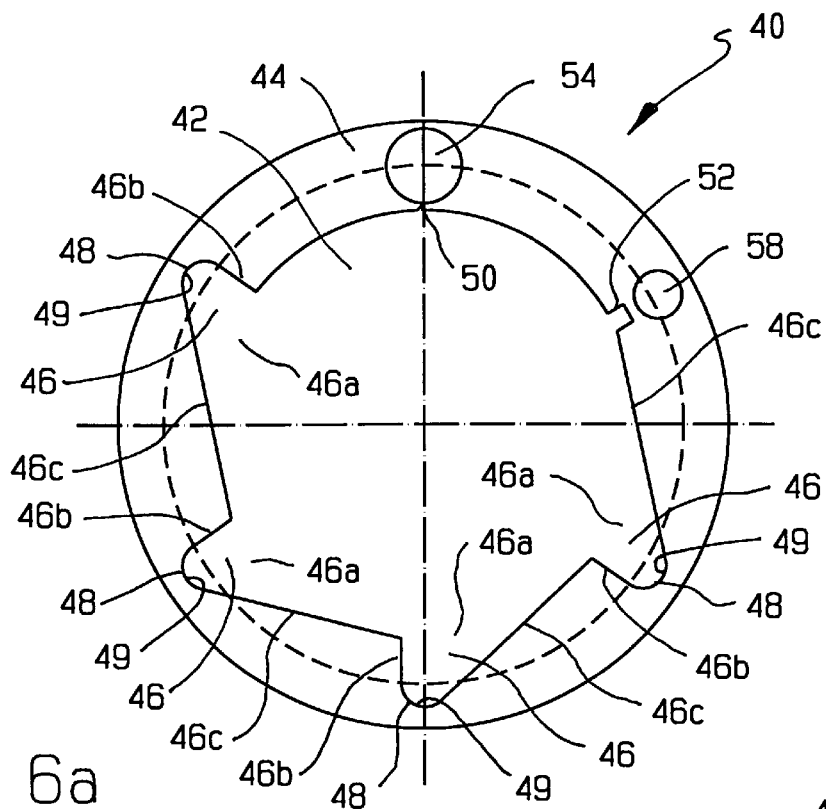
FIGS. 6a and 6b are top and side views of the camplate in the self-contained assay device in FIG. 1.
Figure 6B:
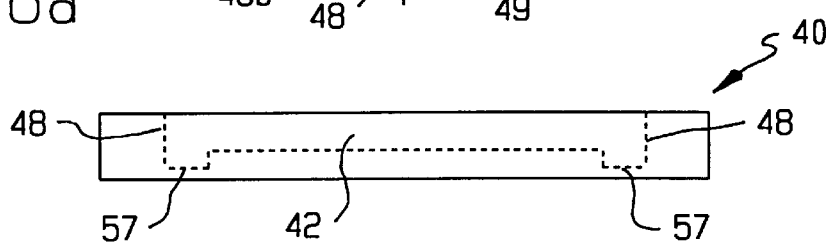

FIGS. 6a and 6b show the cam-plate 40, which is configured as a circular disk made of plastic material, such as clear acrylic. The peripheral of the cam-plate 40 is dimensioned to be tightly fit in the upstanding circular wall 14 of the first housing 10. There is a concave portion 42 formed on the underside of the cam-plate 40 which is surrounded by a rim portion 44 of the cam-plate 40. The concave portion 42 is adapted to accommodate the center portion 22a of the specimen holder 20 while the rim portion 44 is supported on the circular flange 22b of the specimen holder 20. In this manner, the cam-plate 40 can lay on the specimen holder 20 when assembled.

A plurality of cam-shaped chambers 46 are provided on the rim portion 44 of the cam-plate 40 and in communication with the concave portion 42. It is preferred that the cam-shaped chambers 46 are continuously and evenly distributed along, at least a portion of, the peripheral of the concave portion 42. Each chamber 46 has a triangular shape with its bottom portion 46a merging into the concave portion 42. The other two sides 46b and 46c of each chamber 46 meet at an apex 48, which is close to the peripheral of the cam-plate 40. One of the two sides 46b and 46c is a radial side 46b extending substantially radially and the other side 46c is a cam side. The radial sides 46b alternate with the cam sides 46c along the peripheral of the concave portion 42 of the chambers 46.

Preferably, at least part of the cam side 46c of each chamber 46 is curved to facilitate the operation of the assay device 1 as will be discussed later. In addition, each chamber 46 preferably has a curved portion 49 near its apex 48 which continues on to the radial side 46b and the cam side 46c. In this manner, the curved apex portion 49 and the cam side 46c of each chamber 46 provide a smooth transition from the apex 48 of the chamber 46 to the radial side 46b of the next chamber 46 as described hereinafter. Further, the curved apex portion 49 also facilitates the accommodation of a reagent packet 90 as will be described hereinafter.

The number of chambers 46 for the self-contained assay device 1 can be up to 6 or more depending on analysis requirements. In a preferred embodiment shown in FIG. 6a, four chambers 46 are provided. These chambers 46 are continuously arranged along the peripheral of the concave portion 42 to occupy about 240° arc thereof. The apexes 48 of two adjacent chambers 46 are spaced from each for about 60° arc of the peripheral of the concave portion 42.

It is also preferred that at least a portion of the periphery of the rim portion 44 is free of any cam-shaped chamber 46 and therefore a retaining mechanism can be provided thereon. As shown in FIG. 6a, a nitch member 50 and a slot member 52 are provided along the periphery of the concave portion 42 and in the rim portion 44. As will be described in detail hereinafter, the nitch member 50 and the slot member 52 are adapted to retain the spring/latch assembly 30 in position at the start and the end of the operation of the assay deice 1 respectively. The nitch member 50 is located next to a radial side 46b of the first chamber 46. The slot member 52 is located next to the cam side 46c of the last chamber 46. In a preferred embodiment, the nitch member 50, the slot member 52 and the cam-shaped chambers 46 are all evenly distributed along the periphery of the concave portion 42.

The cam-plate 40 also has an opening 54 located on its rim portion 44, through which a specimen to be tested is introduced into the self-contained assay device 1. A filter member (not shown) can be affixed to the opening 54 for filtering debris or the like from the specimen. The opening 54 is preferably aligned with the start position of the assay device 1. It is also preferred that the opening 54 and the cam-shaped chambers 46 are evenly distributed along the periphery of the concave portion 42. In a preferred embodiment shown in FIG. 6a, the opening 54 is in the form of a through hole. The arc between the through hole 54 and one of its adjacent chambers 46 is also 60°. The through hole 54 and the nitch member 50 are substantially in the same radial direction. The through hole 50 is also adapted to receive a receptacle 56 (FIG. 1) therein.

In a preferred embodiment as shown in FIG. 6b, each cam-shaped chamber 46 has a recess portion 57 at its curved apex portion 49. Such a recess portion 57 is dimensioned to contain a reagent packet 90 such as a capsule 90 therein and thus facilitates to retain the capsule 90 in place as will be described later.

The cam-plate 40 can further have an observation port 58 (FIG. 6a) provided on its rim portion 44. The observation port 58 is preferably spaced away from the center of the cam-plate 40 for such a distance that it can be aligned with the position 28 on the specimen holder 20. Further, the observation port 58 and the slot member 52 on the cam-plate 40 are substantially in the same radial direction. In a preferred embodiment, the arc between the observation port 58 and its adjacent chamber 46 is also 60°. The observation port 58 can be in the form of a through hole.

Figure 7:
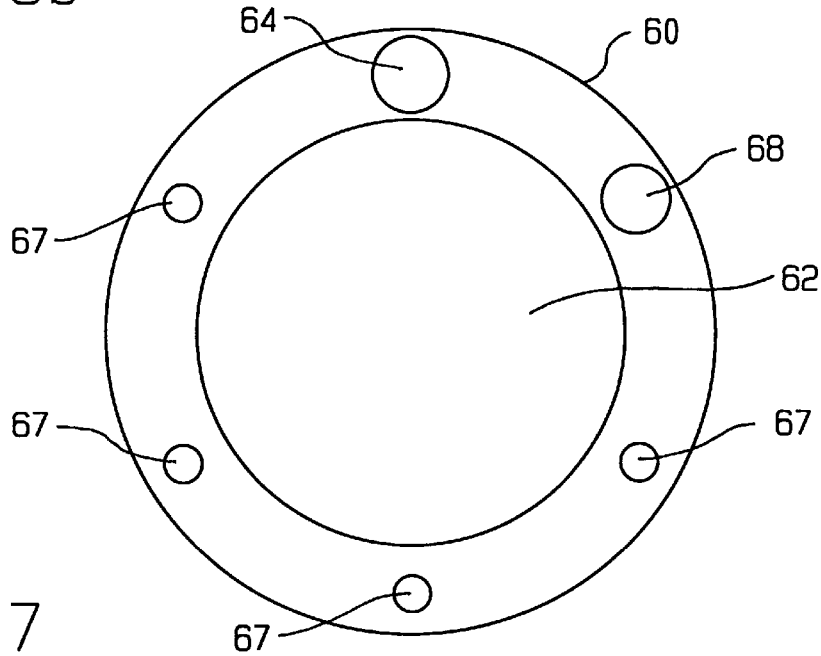
FIG. 7 is a top view of the retaining plate in the self-contained assay device in FIG. 1.

FIG. 7 shows an alternative structure for retaining reagent packet 90 in place. A retaining plate 60 is provided which has a hollowed-out center 62 forming a donut shape. The hollowed-out center 62 of the retaining plate 60 is adapted to loosely fit onto the center portion 22a of the specimen holder 20 so that the retaining plate 60 lays on top of the circular flange 22b upon assembly. An opening portion 64 is provided on the retaining plate 60 for passing the added specimen therethrough and onto position 28 of the specimen holder 20 at a start position of the assay device 1.

The retaining plate 60 has a plurality of through holes 67 thereon. Each through hole 67 corresponds to the location of a curved apex portion 49 on the cam-plate 40 upon assembly. Thereby, the through holes 67 can assist in retaining reagent packets, such as capsules 90, in place and allow released reagents to pass through and onto the specimen holder 20 at position 28. In the embodiment illustrated, four holes 67 are formed on the retaining plate 60, each of which can hold one reagent packet 90.

The retaining plate 60 can also have an observation port 68 thereon, which can be aligned with position 28 at an end position of the assay device 1. In the embodiment as shown in FIG. 7, the observation port 68 on the retaining plate 60 is spaced away from its adjacent through hole 67 for about 60°. The observation port 68 can be in the form of a through hole.

Figure 8A:
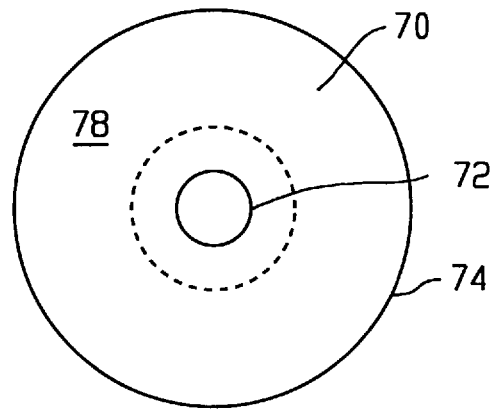
FIGS. 8a and 8b are top and side views of the knob member in the self-contained assay device in FIG. 1.
Figure 8B:
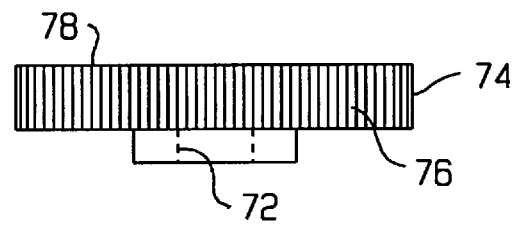

FIGS. 8a and 8b show a knob member 70, which can facilitate the rotation between the specimen holder 20 and the cam-plate 40. The knob member 70 has a through hole 72 therein which can fixedly engage with the pin member 24 on the specimen holder 20 through conventional means such as adhesion. The peripheral 74 of the knob member 70 provides the user with grip mechanism in operating the assay device 1. In a preferred embodiment, the peripheral 74 has straight knurls 76 thereon for assisting the user in gripping the knob member 70. Alternatively, the peripheral 74 of the knob member 70 cam be scalloped. The configuration of the peripheral 74 of the knob member 70 can be various shapes, such as circle, triangle, rectangle, pentagon and hexagon. The knob member 70 can also have an irregular shaped peripheral 74 SO long as the peripheral 74 can provide grip mechanism. It is preferred that the knob member 70 has a flat bottom 78 SO that, when it is attached to the axal 24 on the specimen holder 20, the entire assay device 1 can sit on a flat supporting surface.

Figure 9:
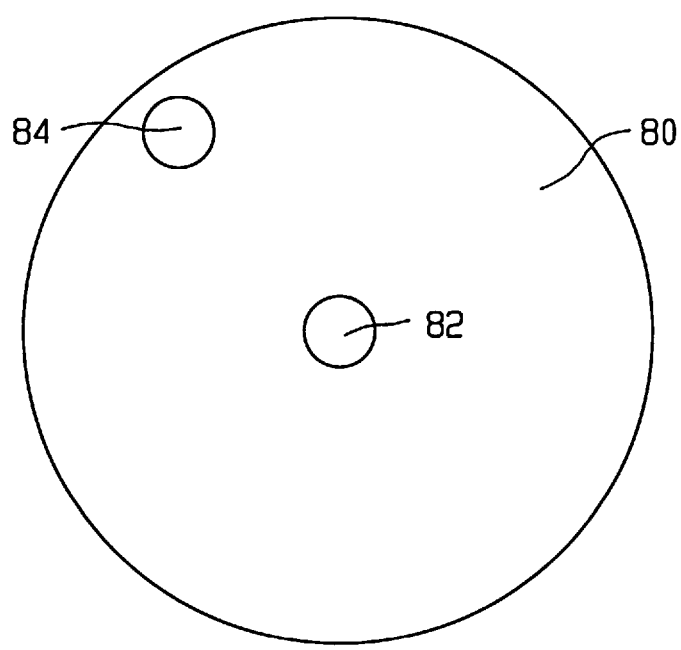
FIG. 9 is a top view of the blotter member in the self-contained assay device in FIG. 1.

FIG. 9 shows a blotter member 80 which can be used in the self-contained assay device 1. The blotter member 80 has a circular shape dimensioned to be tightly fit in the upstanding wall 14 of the first housing 10. The blotter member 80 has a center aperture 82 designed to pass the pin member 24 of the specimen holder 20 therethrough. Thereby, the blotter member 80 can be held between the first housing and the specimen holder 20 when the assay device 1 is assembled. One main function for the blotter member 80 is to absorb excess liquid or any liquid that may leak into the first housing 10 and to prevent the same from leaking out of the self-contained assay device 1.

Further, the blotter member 80 can have a through hole 84 as shown in FIG. 9. The through hole 84 is located near the periphery of the blotter member 80 and away from the center of the blotter member 80 for a distance. Such a distance is substantially the same to that the position 28 is away from the center of the specimen holder 20. Thereby, as the assay device 1 is rotated to its end position, the through hole 84 on the blotter member 80 can be aligned with the position 28 for observation purpose. The use of such through hole 84 is particularly applicable for the case where the first and second housings 10 and 40 and the specimen holder 20 are all made of non-transparent materials. When being used, such blotter member 80 is made aligned with the slot member 52 on the cam-plate 40 and is preferably fixed to the first housing 10.

When assembled, the blotter member 80, the specimen holder 20, the spring/latch assembly 30 and the cam-plate 40 are all accommodated in the first housing 10. The cam-plate 40 is fixedly fit with the first housing 10. The specimen holder 20 is adapted to be rotatable relative to the cam-plate 40 but retained in a start position through the engagement between the latch tip portion 38 and the nitch member 50 on the cam-plate 40. The spring/latch assembly 30 is maintained in a compressed position. Reagent packets 90 containing various reagent(s) and/or wash solution(s) for the test analysis or analyses are placed and retained in the curved apex portions 49 of the chamber 46. The receptacle 56 is attached to the opening 54 on the cam-plate 40 for receiving a specimen to be tested in the assay device 1.

Descriptions will now be made with regard to the operation of the self-contained assay device 1 of the present invention. The assay device 1 is first adjusted to its start position where position 28 on the specimen holder 20 aligns with the opening 54 on the cam-plate 40. A sufficient volume of a specimen to be tested is added into the assay device 1 through the opening 54 on the cam-plate 40 so that it covers completely or wets the position 28 on the specimen holder 20 or the membrane member 29. In a preferred embodiment, the specimen is added into the assay device 1 and evenly distributes on the circular flange 22b of the specimen holder 20 at position 28. In other words, the added specimen is deposited on the membrane member 29.

The specimen holder 20 is then rotated relatively to the cam-plate 40 so that the spring/latch assembly 30 as well as position 28 on the specimen holder 20, leaves the start position and moves toward the first chamber 46. During such rotation, the spring member 32 of the spring/latch assembly 30 is retained in a compressed state through the restriction exerted on tip portion 38 of the latch member 34 by the periphery of the concave portion 42 of the cam-plate 40.

When the spring/latch assembly 30 arrives at the first chamber 46a where the peripheral of the concave portion 42 discontinues, restriction on the compressed spring 32 is released. The latch member 34 then thrusts radially outwardly and into the first chamber 46 till the tip portion 38 of the latch member 34 reaches the curved apex portion 49a of the first chamber 46a. The tip portion 38 thus breaks the capsule 90 retained thereat to release the reagent contained in the capsule 90. The released reagent thus flows into the first chamber 46a and deposits on the circular flange 22b of the specimen holder 20 at the position 28 where the member 29 is attached. The reagent can thus react with the specimen on membrane member 29 at position 28 on the specimen holder 20.

After the reaction, unbound specimen or reagent will pass through the membrane member 29, and/or the porous position 28 on the circular flange 22b and deposit on the blotter member 80. The bound specimen or reagent, on the other hand, is immobilized by the membrane member 29 on the specimen holder 20 for a subsequent assay reaction.

In an embodiment where the rim portion 44 and the circular flange 22b are water-tightly engaged, the unbound specimen or reagent may also be carried away by the first chamber 46a upon further rotation of the assay device 1 to the next reaction position. Alternatively, when the rim portion 44 and the circular flange 22b do not have a water-tight engagement, unbound specimen or reagent can flow therebetween and deposit onto the blotter member 80.

The specimen holder 20 is then rotated again relative to the cam-plate 40 so that the spring/latch assembly 30 and the position 28 on the specimen holder 20 leave the apex portion 48 of the first chamber 46a and move along the cam side 46c toward the second chamber 46b. As the specimen holder 20 is rotated, the cam side 46c of the first chamber 46a pushes the latch member 34 and, in turn, the spring member 32 of the spring/latch assembly 30 back into the slot 26 on the specimen holder 20 and in a compressed state. The spring/latch assembly 30 is thus ready for the next thrust. After the spring/latch assembly 30 is forced back into the slot 26, the result of the reaction can be easily observed through the transparent cam-plate 40.

The above steps are repeated until the latch remote end 36 of the spring/latch assembly 30 passes all the cam-shaped chambers 46 and comes to the end position to engage with the slot member 52. Thereby, the result of a previous reaction is made to react with the reagent and/or wash solution (see below) contained in a next capsule 90 which is retained in a next chamber 46. In this way, the specimen is carried through a series of reactions in an analysis for detecting analyte(s) contained therein. The final result of the test can be easily observed through the transparent cam-plate 40, or through the observation ports 18, 58, 68 and 84. After the test, the assay device 1 can be discarded and no cleaning step is necessary.

In a preferred embodiment, one or more capsules 90' containing a wash solution, i.e., "cleaning capsules" are used in the self-contained assay device 1. Such cleaning capsules 90' are arranged at the curved apex portions 49 of desired cam-shaped chambers 46. In another preferred embodiment, cleaning capsules 90' alternate with the capsules 90 containing reagent(s). Thereby, after each reaction of the reagent 90 and the specimen, a cleaning capsule 90' is broken to release a cleaning agent or wash solution to wash away any unbound specimen or reagent. In this way, only the bound resultant is left at the position 28 or the membrane member 29 on the specimen holder 20, which is to be used for the next assay reaction with the reagent in the next reagent capsule 90.

The assay device of the present invention is useful to determine the presence (or absence) of an analyte in a sample or specimen suspected of containing the analyte. Any type of specimen or sample in fluid form can be used, including but not limited to biological samples such as blood, serum, plasma, milk, urine, sweat, saliva, cerebrospinal fluid, amniotic fluid, semen, vaginal and cervical secretions, broncheal secretions, intestinal fluid, wound fluid (exudates and transudates), thoracentesis fluid, cell or tissue suspensions, etc., environmental samples such as water samples, -soil suspensions, etc.

As used according to the present invention, an analyte is intended to mean any compound or composition to be assessed which is a member of a specific binding pair and may be a ligand or a receptor. A member of a specific binding pair is one of two different compounds or compositions, having an area, either on the surface or in a cavity, which specifically binds to and is thereby defined as complementary with a particular spatial and polar organization of the other compound or composition. The members of a specific binding pair are generally referred to as "ligand" and "receptor" ("anti-ligand").

As used herein, a ligand includes any compound or composition for which a receptor naturally exists or can be prepared. Illustrative ligands include but are not limited to antigens; hormones; pheromones; signal substances such as neurotransmitters, signal proteins and peptides, etc.; enzyme substrates and cofactors; ligands for receptor proteins; nucleic acids and polynucleotides; biotin; lectins; growth factors or cytokines; drugs; toxins; etc.

As used herein, a receptor (anti-ligand) includes any compound or composition which recognizes a particular spatial and polar organization of a compound or composition, e.g., an epitopic or determinant site or a complementary binding site. Illustrative receptors include but are not limited to immunoglobulins or antibodies or antigen binding portions thereof such as Fv, $F(ab')_2$, Fab fragments, single chain antibodies, chimeric or humanized antibodies, complementary determining regions of antibodies; hormone receptors; pheromone receptors; signal substance receptors; enzymes; protein receptors; nucleic acids and polynucleotides; avidin or streptavidin; lectin binding proteins; growth factor or cytokine receptors; drug receptors; etc. As will be understood easily by those skilled in the art, nucleic acids, polynucleotides and oligonucleotides which are complementary to one another can serve as the two members of a specific binding pair which can be used in the assay devices of the present invention, one serving as ligand and the other serving as receptor or anti-ligand.

When the analyte to be detected is an antigen associated with an infectious agent such as a bacterium, fungus, virus, mycoplasma or other parasite, the assay device of the invention can be used for the detection of infectious disease in a patient from which the sample or specimen is obtained. When the analyte to be detected is an antibody against an antigen associated with an infectious agent, the assay device of the invention can be used to detect the presence of immunity to an infectious disease in the patient from whom the specimen is obtained. In this instance, the signal detected can be compared to a standard provided, and immunity is assessed by comparison to appropriate signal, e.g., color developed, indicating at least a minimum antibody titer present. In one embodiment, the standard can be provided as appropriate zone(s) 29b (see FIG. 4a) on the membrane member 29. The two above-described uses of the present device are only illustrative examples. Numerous other uses for the assay devices of the invention will occur to those skilled in the art depending upon the analyte to be detected, including but not limited to detection of the presence or absence of particular types of cancer, genetic mutations or defects, metabolic imbalances, drugs, toxins, pesticides, etc. and are all within the scope of the applications or methods for using the present invention.

The reagents and/or wash solutions, optionally including an ancillary material such as a buffer, stabilizer, additive to enhance binding, etc., contained in the assay device as well as the amount of reagent retained in the reagent packets 90 of the assay device will depend upon the analyte to be detected and is readily known to those skilled in the art.

In all instances, there is at least one reagent packet 90 which contains a reagent which is complementary to and binds specifically to the analyte(one member of a specific binding pair) which is to be tested for in the assay, i.e., the other member of the specific binding pair.

In all instances, there is provided at least one or more of the reagents which provides a signal system, such as a color change, which indicates the presence of the analyte in the specimen being tested. One reagent which is a member of the specific binding pair which binds specifically to the analyte, i.e., second specific binding pair member, or another molecule which binds specifically to the second binding pair member is labelled to provide a signal system. Suitable signal systems employ the use of an enzyme label, a fluorescent label, a chemiluminescent label or enhanced chemiluminescent label, or a radioactive label, etc. Non-radioactive labels are preferred. Suitable signal systems are well-known to those skilled in the art. See, for example, David Wild, ed., The Immunoassay Handbook, Stockton Press, 1994, particularly at pages 63–77 (incorporated herein by reference) for suitable labels and signal generation systems useful when the specific binding pair members are antigen and antibody (or binding portion thereof). See, for example, George H. Keller et al., DNA Probes, Stockton Press, 1989, particularly at pages 71–148 (incorporated by reference herein) for suitable labels and signal generation systems when the specific binding pair members are complementary polynucleotides.

Preferred are signal systems in which a change, such as in color, indicating the presence of analyte in a specimen can be detected visually by the naked eye of the person using the assay device under normal ambient conditions.

As one illustrative example, when the analyte to be detected is an antigen suspected of being present in a patient specimen, the reagents retained in the assay device 1 can include a capture anti-antigen antibody bound to the reaction membrane member, a second anti-antigen antibody that recognizes a different epitope from that recognized by the capture antibody labelled, e.g. with an enzyme such as horseradish peroxidase; a wash solution, and a substrate for the enzyme label, e.g., 2,2'-azino-bis (ethylbenzothiazoline-6-sulfonate) (ABTS), D-phenylenediamine (OPD) or (3,3', 5,5'-tetramethyl benzidine (TMB) (all peroxidase substrates). Alternatively, the reagents for such assay can include a capture antibody, an anti-antigen antibody; a wash solution; an anti-antibody labelled e.g., with an enzyme; a wash solution and a substrate for the enzyme label.

As another illustrative example, when the analyte to be detected is an antibody suspected of being present in a patient specimen, the reagents retained in the assay device 1 can include an antigen to which the suspected antibody binds specifically bound to the reaction membrane member; a wash solution; anti-immunoglobulin, e.g., human immunoglobulin labelled e.g., with an enzyme label; a wash solution; and a substrate for the enzyme label which when reacted with the enzyme provides a detectable color change indicating presence of the analyte.

According to an embodiment of the present invention, illustrated in FIG. 4a a predetermined amount of the analyte to be detected is immobilized on a predetermined portion of the membrane member 29, i.e., 29b, provided on the circular flange 22b of the specimen holder 20 at position 28. The predetermined amount of immobilized analyte reacts with all the reagents 90 and affords a positive analyte control that provides a positive control signal indicating that the reagents are functioning properly and assuring the user of the device that the assay has been successfully conducted.

The following illustrative example describes a method for detecting an analyte which is an antigen, e.g. a hepatitis A antigen, suspected of being present in a patient using the self-contained assay device of the present invention. The example is for illustrative purposes only and is in no way intended to limit the scope of the methods of the invention or the appended claims. As will be appreciated by those skilled in the art, the methods for using the self-contained assay device can be modified or changed for use to assay for numerous other analytes and all such modifications or changes may be practiced and are encompassed within the scope of the appended claims.

As an example, the method for detecting hepatitis antigen comprises: introducing a predetermined quantity of a specimen which is a patient blood sample into the self-contained assay device of the present invention through the opening 54 on the cam-plate 40, said assay device having a number of reagents immobilized onto separate portions of the membrane member 29, i.e., 29b, positioned on the specimen holder 20 onto which the blood sample is introduced; the membrane member 29 at specific areas and zones 29b having immobilized thereon the following substances: hepatitis A viral antigen (positive control), unrelated protein such as gelatin (negative control), anti-hepatitis A antibody (capture antibody), anti-hepatitis C antibody and anti-hepatitis B antibody respectively; rotating the specimen holder 20 relative to the cam-plate 40 to move the latch member 34 and the spring member 32 of the spring/latch assembly 30 from a start position toward a first chamber 46 till the latch remote end 36 reaches the apex portion 48 of the first chamber to dispense a wash solution to wash away any unbound material; rotating the specimen holder 20 relative to the cam-plate 40 to move the spring/latch assembly 30 to the next chamber 46 to dispense a reagent 90 containing an anti-hepatitis A antibody that recognizes an epitope different from the one recognized by the capture antibody, labelled with an enzyme label; permitting the released antibody to contact the specimen on the membrane member for a sufficient time so that any antigen present can bind to the enzyme labelled antibody; rotating the specimen holder 20 relative to the cam-plate 40 to move the latch member 34 and the spring member 32 of the spring/latch assembly 30 to the next chamber 46 to dispense a reagent 90 retained therein releasing a wash solution; repeating the above step till the latch remote end 36 of the spring/latch assembly 30 reaches the next chamber 46 and dispenses a reagent 90 retained therein releasing a substrate for the enzyme (label) and permitting reaction to occur between any enzyme labelled antibody bound to the specimen holder 20 and the enzyme substrate to provide a color change indicative of the presence of antigen; and rotating the specimen holder 20 relative to the cam-plate 40 to move the latch member 34 and the spring member 32 of the spring/latch assembly 30 from the last chamber 46 to an end position; and observing the results, comparing the color signal developed on the portion of the membrane member 29 to which the specimen was applied with that of the portion of the membrane member 29b on which hepatitis A was immobilized as a positive control to determine whether hepatitis A is present in the patient sample.

In another embodiment, the self-contained assay device 1 can be used to detect the presence of more than one analyte in a sample. In a preferred mode of this embodiment of the invention, the assay device 1 can be used to detect the presence of a number of antibodies to a number of infectious agents to assess whether a patient has sufficient immunity to each of the various infectious agents.

As an illustrative example, the assay device 1 as shown in FIGS. 1–9 can be used to detect antibodies against a panel of viral agents, e.g., measles, mumps and rubella, etc. in order to assess the status of vaccination against each such virus. A sufficient amount of specimen is applied to wet or to cover the membrane member 29. The membrane member 29 at specific areas or zones 29b contains the following substances: human serum immunoglobulins (positive control), gelatin, an unrelated protein (negative control), measles antigen, mumps antigen, and rubella antigen, respectively. As will be understood by those skilled in the art, the position and/or configuration of each of the positive and negative controls and of each of the antigens on the membrane member is identified to help easily determine which one or more antibodies is/are present in the specimen. See, for example, FIG. 4a. The specimen is permitted to contact the membrane member 29 for a time sufficient for any antibody in the specimen to bind to the immobilized antigen(s). The first chamber 46 retains wash solution to wash away any unbound antibody. The next-chamber 46 retains anti-human immunoglobulin labelled with an enzyme label. The next chamber 46 retains a wash solution to wash away any unbound labelled antibody. The next chamber 46 retains enzyme substrate, which provides a color change when reacted with enzyme (labelled antibody). Thus, when the assay is completed, visualization of the results is easily provided to determine the presence or absence of each of measles, mumps and rubella antibodies in the patient specimen.

The foregoing description is only illustrative of the principle of the present invention. It is to be recognized and understood that the invention is not to be limited to the exact configuration as illustrated and described herein. Accordingly, all expedient modifications readily attainable by one versed in the art from the disclosure set forth herein that are within the scope and spirit of the present invention are to be included as further embodiments of the present invention. The scope of the present invention accordingly is to be defined as set forth in the appended claims.

What is claimed is:

1. A self-contained assay device comprising:
   (a) a first housing having a bottom with a center hole;
   (b) a specimen holder rotatably fit in the first housing and including a center portion with a center and a peripheral, a circular flange surrounding the center portion and a pin member extending from the underneath of the center portion, the center portion having a radial slot extending from its peripheral toward its center;
   (c) a spring/latch assembly adapted to be held in the slot on the specimen holder and including a spring member disposed near the center of the center portion and a latch member having a remote end; and
   (d) a second housing fixedly fit in the first housing and comprising:
      a rim portion surrounding a concave portion adapted to accommodate the center portion of the specimen holder;
      an opening on the rim portion for adding a specimen to be tested; and
      a plurality of cam-shaped chambers provided in the rim portion and communicating with the concave portion, each cam-shaped chamber having an apex portion located furthest away from the concave portion and a cam side extending from the apex portion toward the next chamber and each chamber having a capsule containing either a reagent or wash solution retained therein,
      when the specimen holder is rotated relative to the cam plate, the remote end of the latch member moves along the rim portion and can be thrust into each chamber to break the capsule retained therein to release a reagent or wash solution for testing analyte (s) in a specimen.

2. The assay device of claim 1 further comprising a membrane member attached to the circular flange of the specimen holder adjacent to the slot, the membrane member being made of a porous material.

3. The assay device of claim 2 wherein the membrane member further comprises a plurality of zones, each of which binds an assay substance.

4. The assay device of claim 1 wherein the circular flange of the specimen includes a reaction position located next to the radial slot.

5. The assay device of claim 4 wherein the reaction position on the circular flange is porous.

6. The assay device of claim 5 further comprising a porous membrane member, the membrane member being attached to the reaction position on the circular flange.

7. The assay device of claim 1 further comprising first and second retainer members located in the rim portion of the cam plate and determining a start position and an end position of the assay device, the first retainer member being in the same radial direction of the opening of the cam plate.

8. The assay device of claim 7 wherein there are four cam-shaped chambers, the apex portions of the chambers and the first and second retainer members being evenly distributed along the rim portion.

9. The assay device of claim 7 wherein the first and second retainer members are nitch and slot members.

10. The assay device of claim 1 wherein the remote end of the latch member is a curved tip portion.

11. The assay device of claim 1 further comprising a blotter member inserted between the bottom of the first housing and the specimen holder.

12. The assay device of claim 1 further comprising a knob member, the knob member having a center hole for fixedly fitting onto the pin member of the specimen holder.

13. The assay device of claim 1 wherein each chamber has a recess portion at its apex portion.

14. The assay device of claim 1 further comprising a retaining plate having a hollowed-out center and adapted to fit onto the circular flange of the specimen holder, the retaining plate having a center hole and a plurality of through holes corresponding to the opening and the apex portions of the cam plate.

15. The assay device of claim 1 wherein the first and the second housings, the specimen holder and the latch member are made of clear plastic.

16. The assay device of claim 7 wherein each of the first and second housings has a through hole adapted to align with the second retainer member at the start position.

17. A method for detecting analyte(s) in a specimen comprising the steps of:
   (a) adding a specimen of a predetermined quantity into the self-contained assay device of claim 1 through the opening on the cam plate;
   (b) rotating the specimen holder relatively to the cam plate to move the spring/latch assembly from a start position toward a first chamber till the spring/latch assembly reaches the first chamber to break a capsule retained therein;
   (c) rotating the specimen holder relatively to the cam plate to move the spring/latch assembly to the next chamber to break a capsule retained therein;
   (d) repeating the above step (c) till the spring/latch assembly reaches the last chamber and breaks a capsule retained therein;
   (e) rotating the specimen holder relatively to the cam plate to move the spring/latch assembly from the last chamber to an end position; and
   (f) observing the results.

* * * * *